(12) United States Patent
Klose et al.

(10) Patent No.: US 7,387,789 B2
(45) Date of Patent: Jun. 17, 2008

(54) TRANSDERMAL DELIVERY OF NON-STEROIDAL ANTI-INFLAMMATORY DRUGS

(75) Inventors: Kathryn Traci-Jane Klose, Bonbeach (AU); Margarita Vladislavova Bakalova, Bundoora (AU); Timothy Matthias Morgan, Carlton North (AU); Barrie Charles Finnin, Glen Iris (AU); Barry Leonard Reed, Strathmore (AU)

(73) Assignee: ACRUX DDS Pty. Ltd., Melbourne (AU)

( * ) Notice: Subject to any disclaimer, the term of this patent is extended or adjusted under 35 U.S.C. 154(b) by 10 days.

(21) Appl. No.: 11/517,575

(22) Filed: Sep. 8, 2006

(65) Prior Publication Data

US 2007/0077288 A1    Apr. 5, 2007

Related U.S. Application Data

(60) Continuation-in-part of application No. 10/759,303, filed on Jan. 20, 2004, which is a continuation-in-part of application No. 09/910,780, filed on Jul. 24, 2001, now Pat. No. 6,818,226, which is a division of application No. 09/125,436, filed as application No. PCT/AU97/00091 on Feb. 19, 1997, now Pat. No. 6,299,900.

(30) Foreign Application Priority Data

Feb. 19, 1996 (AU) ................ PN8144/96

(51) Int. Cl.
*A62K 9/70* (2006.01)
*A61K 31/21* (2006.01)
*A01N 37/00* (2006.01)

(52) U.S. Cl. ........................ 424/449; 514/506

(58) Field of Classification Search ............. 424/449; 514/506
See application file for complete search history.

(56) References Cited

U.S. PATENT DOCUMENTS 3,306,252 A    2/1967    Knight et al.

(Continued)

FOREIGN PATENT DOCUMENTS

AU    30258/89    9/1989

(Continued)

OTHER PUBLICATIONS

Bucks et al., Percutaneous Absorption of Hydroquinone in Humans: Effect of 1-Dodecylazacycloheptan-2-One (Azone) and the 2-Ethylhexyl Ester of 4-(Dimethylamino) Benzoic Acid (Escalol 507), Journal of Toxicology and Environmental Health, 24:279-289 (1988).

(Continued)

*Primary Examiner*—Johann Richter
*Assistant Examiner*—Konata M. George
(74) *Attorney, Agent, or Firm*—Foley & Lardner LLP

(57) ABSTRACT

The present invention provides a transdermal drug delivery system which comprises: a therapeutically effective amount of a non-steroidal anti-inflammatory drug; at least one dermal penetration enhancer, which is a safe skin-tolerant ester sunscreen ester; and at least one volatile liquid. The invention also provides a method for administering at least one systemic or locally acting non-steroidal anti-inflammatory drug to an animal which comprises applying an effective amount of the non-steroidal anti-inflammatory drug in the form of the drug delivery system of the present invention.

19 Claims, 2 Drawing Sheets

U.S. PATENT DOCUMENTS

| | | | |
|---|---|---|---|
| 3,989,816 A | 11/1976 | Rajadhyaksha | |
| 4,299,826 A | 11/1981 | Luedders | |
| 4,310,511 A | 1/1982 | Holick | |
| 4,440,777 A | 4/1984 | Zupan | |
| 4,557,934 A | 12/1985 | Cooper | |
| 4,563,346 A | 1/1986 | Deckner | |
| 4,663,157 A | 5/1987 | Brock | |
| 4,699,779 A | 10/1987 | Palinczar | |
| 4,704,406 A | 11/1987 | Stanisiaus et al. | 514/570 |
| 4,820,724 A | 4/1989 | Nimni | |
| 4,938,951 A | 7/1990 | Leung et al. | |
| 4,946,671 A | 8/1990 | Bissett et al. | |
| 4,954,487 A | 9/1990 | Cooper et al. | |
| 4,959,205 A | 9/1990 | Brunner et al. | |
| 4,975,272 A | 12/1990 | Voyt | |
| 5,030,442 A | 7/1991 | Uster et al. | |
| 5,034,386 A | 7/1991 | Peck et al. | 514/212 |
| 5,036,100 A | 7/1991 | Deboeck et al. | |
| 5,082,866 A | 1/1992 | Wong et al. | 514/785 |
| 5,100,918 A | 3/1992 | Sunshine et al. | |
| 5,122,519 A | 6/1992 | Ritter | |
| 5,192,534 A | 3/1993 | Grollier et al. | |
| 5,256,647 A | 10/1993 | Minaskanian et al. | 514/24 |
| 5,413,794 A | 5/1995 | Suzuki et al. | |
| 5,426,210 A | 6/1995 | Kato et al. | |
| 5,446,025 A | 8/1995 | Lu et al. | |
| 5,449,519 A | 9/1995 | Wolf et al. | |
| 5,487,898 A | 1/1996 | Lu et al. | |
| 5,573,754 A | 11/1996 | Kulkarni et al. | |
| 5,674,912 A | 10/1997 | Martin | |
| 5,679,374 A | 10/1997 | Fanchon et al. | |
| 5,804,168 A | 9/1998 | Murad | 424/439 |
| 5,951,967 A | 9/1999 | Golz et al. | |
| 6,004,969 A | 12/1999 | Hu | |
| 6,010,716 A | 1/2000 | Saunal et al. | |
| 6,211,250 B1* | 4/2001 | Tomlinson et al. | 514/772.4 |
| 6,299,900 B1* | 10/2001 | Reed et al. | 424/449 |
| 6,818,226 B2* | 11/2004 | Reed et al. | 424/449 |
| 6,916,486 B2 | 7/2005 | Klose et al. | |
| 6,916,487 B2 | 7/2005 | Klose et al. | |
| 6,923,983 B2 | 8/2005 | Morgan et al. | |
| 6,929,801 B2 | 8/2005 | Klose et al. | |
| 2004/0096405 A1 | 5/2004 | Chew et al. | |
| 2004/0146469 A1 | 7/2004 | Reed et al. | |
| 2005/0186141 A1* | 8/2005 | Gonda et al. | 424/45 |

FOREIGN PATENT DOCUMENTS

| | | |
|---|---|---|
| AU | 49984/1990 | 9/1989 |
| AU | A-30258/89 | 9/1989 |
| AU | A-49984/90 | 9/1990 |
| AU | 91413/91 | 6/1992 |
| CA | 2 218 534 | 6/1996 |
| DE | 43 34 553 | 4/1995 |
| EP | 0 189 861 | 8/1986 |
| EP | 189 861 | 8/1986 |
| EP | 0 332 147 | 9/1989 |
| EP | 0 552 405 | 7/1993 |
| EP | 0 552 405 A1 | 7/1993 |
| EP | 0 581 587 A2 | 2/1994 |
| EP | 0 614 354 B1 | 9/1994 |
| EP | 0608 322 B1 | 7/1998 |
| JP | 61-268631 | 11/1986 |
| WO | WO 92/10154 | 6/1992 |
| WO | 92/19271 | 11/1992 |
| WO | WO 92/20376 A1 | 11/1992 |
| WO | WO 93/10755 A1 | 6/1993 |
| WO | WO 96/17624 | 6/1996 |
| WO | 96/30000 | 10/1996 |
| WO | WO 96/41613 | 12/1996 |

OTHER PUBLICATIONS

Physicians' Desk Reference (49 Ed.) 1995, pp. 1151-1152, Medical Economics Company, Inc., Montvale, N.J.

R. J. Feldmann et al., "Percutaneous Penetration of 14C Hydrocortisone In Man", *Arch Derm*, vol. 94:649-651, (1966).

M. F. Coldman et al., "Enhancement Of Percutaneous Absorption by The Use Of Volatile: Nonvolatile Systems And Vehicles", *Journal of Pharmaceutical Sciences*, vol. 58(9):1098-1102, (1969).

P. P. Bhatt, et al., "Finite Dose Transport Of Drugs In Liquid Formulations Through Stratum Corneum: Analytical Solution To A Diffusion Model", *International Journal Of Pharmaceutics*, Elsevier science Publishers B. V., vol. 50:197-203, (1989).

Nimni, U.S. Patent No. 4,820,742, Internet: www.patents.ibm.com/fegi-bin/any2htm Document "Dual phase Solvent Carrier System", pp. 3, 4 and 6 out of 7 pages.

Good et al., "A New Transdermal Delivery System for Estraiol," Journal of Controlled Release 2:89-97 (1985) © Elsevier Science Publishers B.V., Amsterdam—Printed in The Netherlands.

\* cited by examiner

TRANSDERMAL DELIVERY OF NON-STEROIDAL ANTI-INFLAMMATORY DRUGS

This application is a continuation-in-part of U.S. patent application Ser. No. 10/759,303 filed Jan. 20, 2004, which is a continuation-in-part of U.S. patent application Ser. No. 09/910,780, now U.S. Pat. No. 6,818,226, filed Jul. 24, 2001, which is a divisional of U.S. patent application Ser. No. 09/125,436, now U.S. Pat. No. 6,299,900, filed Dec. 18, 1998 as the U.S. national stage application of PCT application PCT/AU97/00091, filed Feb. 19, 1997. The entire contents of each of U.S. patent application Ser. No. 10/759,303, U.S. Pat. No. 6,818,226, U.S. Pat. No. 6,299,900, and PCT application PCT/AU97/00091 are incorporated herein by reference, and priority to each is claimed under 35 U.S.C. §119 and/or §120.

FIELD OF THE INVENTION

The present invention relates to transdermal drug delivery. More specifically, the invention relates to a topical absorption/penetration enhancing agent for use in the delivery of non-steroidal anti-inflammatory drugs and non-steroidal anti-inflammatory drug derivatives to an animal, including a human. The invention also relates to a system for the non-occlusive delivery to an animal of non-steroidal anti-inflammatory drugs and non-steroidal anti-inflammatory drug derivatives across a dermal surface of the animal. Transdermal drug formulations of the present invention may be used for local application or systemic delivery.

BACKGROUND OF THE INVENTION

There is a constant need for methods for the safe and effective administration of physiologically active agents, such as non-steroidal anti-inflammatory drugs. For many medications it is important that the administration regime is as simple and non-invasive as possible in order to maintain a high level of compliance by a patient. Oral administration is one administration regime that is commonly used because it is a relatively simple regime to follow. However, the oral administration route is also complicated because of complications associated with gastrointestinal irritation and with drug metabolism in the liver.

Administration of physiologically active agents through the skin ('transdermal drug delivery') has received increased attention because it not only provides a relatively simple dosage regime but it also provides a relatively slow and controlled route for release of a physiologically active agent into the systemic circulation. However, transdermal drug delivery is complicated by the fact that the skin behaves as a natural barrier and therefore transport of agents through the skin is a complex mechanism.

Structurally, the skin consists of two principle parts, a relatively thin outermost layer (the 'epidermis') and a thicker inner region (the 'dermis'). The outermost layer of the epidermis (the 'stratum corneum') consists of flattened dead cells which are filled with keratin. The region between the flattened dead cells of the stratum corneum are filled with lipids which form lamellar phases that are responsible for the natural barrier properties of the skin.

For effective transdermal delivery of a physiologically active agent that is applied to the surface of the skin ('topical application'), the agent must be partitioned firstly from the vehicle into the stratum corneum, it must typically then be diffused within the stratum corneum before being partitioned from the stratum corneum to the viable epidermis and then into the dermal circulation.

To overcome some of the problems with transdermal delivery that are associated with transport across the dermal layers ('percutaneous absorption'), physiologically active agents are commonly formulated with incorporation of one or more dermal penetration enhancers (Finnin and Morgan, J. Pharm. Sci., Vol 88, No. 10, October 1999, pp. 955-958) which are often lipophilic chemicals that readily partition into the stratum corneum whereupon they exert their effects on improving the transport of drugs across the skin barrier.

There is a need for improvements in the transdermal delivery of non-steroidal anti-inflammatory drugs.

SUMMARY OF THE INVENTION

According to the present invention there is provided a transdermal drug delivery system comprising:
(a) a therapeutically effective amount of a non-steroidal anti-inflammatory drug;
(b) at least one dermal penetration enhancer, which is a safe skin-tolerant ester sunscreen of formula (I):

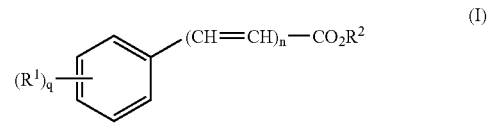

wherein
R$^1$ is hydrogen, lower alkyl, lower alkoxy, halide, hydroxy or NR$^3$ R$^4$;
R$^2$ is a C$_8$ to C$_{18}$ alkyl;
R$^3$ and R$^4$ are each independently hydrogen, lower alkyl or R$^3$ and R$^4$ together with the nitrogen atom to which they are attached form a 5- or 6-membered heterocyclic ring;
n is 0 or 1, and
q is 1 or 2,
wherein, when n is 0 and R$^1$ is NR$^3$ R$^4$, then NR$^3$ R$^4$ is para-substituted, and
wherein said dermal penetration enhancer is present in an amount of from about 10 to about 10,000 wt % based on the weight of the non-steroidal anti-inflammatory drug; and
(c) at least one volatile liquid.

In addition to providing improved percutaneous absorption efficiency, the composition of the invention may also provide lower irritancy than some other more occlusive delivery systems such as transdermal patches, because the composition is non-occlusive to the skin.

More preferably the dermal penetration enhancer is selected from the group consisting of a C$_8$ to C$_{18}$ alkyl para-aminobenzoate, C$_8$ to C$_{18}$ alkyl dimethyl-para-aminobenzoate, C$_8$ to C$_{18}$ alkyl cinnamate, C$_8$ to C$_{18}$ alkyl methoxycinnamate or C$_8$ to C$_{18}$ alkyl salicylate. Most preferably the dermal penetration enhancer is octyl salicylate (2-ethylhexyl salicylate, octisalate), octyl dimethyl para-aminobenzoate or octyl para-methoxycinnamate (Padimate O).

The drug delivery systems according to the invention may comprise one or more non-steroidal anti-inflammatory drugs together with the penetration enhancer incorporated into a dosage form for topical application to the skin of animals. Suitable dosage forms include creams, lotions, gels, ointments, mousses, sprays, aerosols, or any one of a variety of transdermal devices for use in the continuous administration of systematically active drugs by absorption through the skin, underlying soft tissue or joints. Some examples of suitable vehicles are given in U.S. Pat. Nos. 3,598,122, 3,598,123, 3,742,951, 3,814,097, 3,921,636, 3,993,072, 3,993,073, 3,996,934, 4,031,894, 4,060,084, 4,069,307, 4,201,211, 4,230,105, 4,292,299, 4,292,303, 5,323,769, 5,023,085, 5,474,783, 4,941,880 and 4,077,407. These disclosures are thus hereby incorporated herein by reference.

Optionally the drug delivery system may contain pharmaceutical compounding agents, such as one or more thickening agents such as cellulosic thickening agents, ethylcellulose, hydroxypropyl cellulose, hydroxypropyl methylcellulose, povidone, polyacrylic acids such as carbopol, Sepigel® (polyacrylamide/isoparaffin/laureth-7), the Gantrez® series of polymethyl vinyl ether/maleic anhydride copolymers such as the butyl ester of PVM/MA copolymer Gantrez® A-425, and any thickening agent known in the art that has good compatibility with the volatile liquid and enhancers of the present invention.

Non-steroidal anti-inflammatory drugs that may be used in the composition of the present invention include any locally or systemically active non-steroidal anti-inflammatory drugs which are compatible with the dermal penetration enhancers of the present invention and which can be delivered through the skin with the assistance of the dermal penetration enhancer to achieve a desired effect. Suitable non-steroidal anti-inflammatory drugs include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, acemetacin, amtolmetin, azapropazone, benorilate, benoxaprofen, benzydamine hydrochloride, bromfenal, bufexamac, butibufen, carprofen, celecoxib, choline salicylate, clonixin, dipyone, droxicam, etodolac, etofenamate, etoricoxib, felbinac, fenbufen, fentiazac, floctafenine, flufenamic acid, indoprofen, isoxicam, lornoxicam, loxoprofen, licofelone, fepradinol, magnesium salicylate, meclofenamic acid, meloxicam, morniflumate, niflumic acid, nimesulide, oxaprozen, piketoprofen, priazolac, pirprofen, propyphenazone, proquazone, rofecoxib, salalate, sodium salicylate, sodium thiosalicylate, suprofen, tenidap, tiaprofenic acid, tolmetin, trolamine salicylate, and zomepirac The non-steroidal anti-inflammatory agent may be a racemic mixture or individual enantiomers where applicable.

In one preferred form of the invention the drug delivery system comprises on a weight basis from about 1 to about 15% of the non-steroidal anti-inflammatory drug, from about 1 to 10% of the at least one dermal penetration enhancer and from about 75 to 98% ethanol, isopropanol or mixture thereof.

In another preferred form of the invention the drug delivery system comprises, on a weight basis, from about 1 to 5% of an non-steroidal anti-inflammatory drug, from about 1 to 5% of at least one dermal penetration enhancer, which is a safe skin-tolerant ester sunscreen, from about 45 to 90% ethanol, isopropanol or mixture thereof, 5 to 45% water; and optionally 0.5 to 5% of a thickening agent.

Whilst it is preferred that the non-steroidal anti-inflammatory drug and penetration enhancer be delivered by simultaneous administration, the penetration enhancer may be applied before or after the application of the non-steroidal anti-inflammatory drug, if desired.

The present invention also provides a method for administering at least one systemic or locally acting non-steroidal anti-inflammatory drug to an animal which comprises applying an effective amount of the non-steroidal anti-inflammatory drug in the form of the drug delivery system of the present invention.

Preferably the animal is a human but the invention also extends to the treatment of non-human animals.

Preferably the drug delivery system is not supersaturated with respect to the non-steroidal anti-inflammatory drug. As the volatile liquid of the drug delivery system evaporates, the resulting non-volatile composition is rapidly driven into the dermal surface. It is possible that as the volatile liquid evaporates, the non-volatile dermal penetration enhancer becomes supersaturated with respect to the non-steroidal anti-inflammatory drug. However, it is preferred that any supersaturation does not occur before transport of the resulting non-volatile composition across the epidermal surface has occurred.

It is most desirable that, after application of the drug delivery system, the volatile component of the delivery system evaporates and the area of skin to which the drug delivery system was applied becomes touch-dry. Preferably said area of skin becomes touch-dry within 10 minutes, more preferably within 3 minutes, most preferably within 1 minute.

The group of dermal penetration enhancing ester sunscreen compounds of the present invention are particularly suitable for transdermal delivery non-steroidal anti-inflammatory drugs through the skin of an animal. These dermal penetration enhancing compounds are of low toxicity to the skin and are excellent promoters of percutaneous absorption.

Preferred volatile liquids of the present invention include safe skin-tolerant solvents such as ethanol and isopropanol. An aerosol propellant, such as dimethyl ether, may constitute a volatile liquid for the purpose of the present invention.

Surprisingly the group of dermal penetration compounds identified enhance the absorption of non-steroidal anti-inflammatory drugs through the skin while avoiding the significant pharmacological disadvantages and toxicities of prior art enhancers. Additionally, the group of compounds of the invention surprisingly exhibit appreciable penetration into and substantivity for the outer layers of the skin, namely the stratum corneum which has previously presented a formidable barrier to percutaneous drug absorption.

In drug delivery systems according to the present invention a pharmaceutical compounding agent, co-solvent, surfactant, emulsifier, antioxidant, preservative, stabiliser, diluent or a mixture of two or more of said components may be incorporated in these systems as is appropriate to the particular route of administration and dosage form. The amount and type of components used should be compatible with the dermal penetration enhancers of this invention as well as with the non-steroidal anti-inflammatory drug. A co-solvent or other standard adjuvant, such as a surfactant, may be required to maintain the non-steroidal anti-inflammatory drug in solution or suspension at the desired concentration.

The pharmaceutical compounding agents can include paraffin oils, esters such as isopropyl myristate, ethanol, silicone oils and vegetable oils. These are preferably used in the range 1 to 50%. Surfactants such as ethoxylated fatty alcohols, glycerol mono stearate, phosphate esters, and other commonly used emulsifiers and surfactants preferably in the range of 0.1 to 10% may be used, as may be preservatives such as hydroxybenzoate esters for preservation of the compound preferably in amounts of 0.01% to 0.5%. Typical co-solvents and adjuvants may be ethyl alcohol, isopropyl alcohol, acetone, dimethyl ether and glycol ethers such as diethylene glycol mono ethyl ether. These may be used in amounts of 1 to 50%.

Because of the effect of the penetration enhancer of the invention, the dosage of the non-steroidal anti-inflammatory drug may often be less than that conventionally used. It is proposed that, a dosage near the lower end of the useful range of the particular non-steroidal anti-inflammatory drug may be employed initially and increased as indicated from the observed response if necessary.

The concentration of non-steroidal anti-inflammatory drug used in the drug delivery system will depend on its properties and may be equivalent to that normally utilised for the particular non-steroidal anti-inflammatory drug in conventional formulations. Both the amount non-steroidal anti-inflammatory drug and the amount of penetration enhancer will be influenced by the type of effect desired.

Where it is desired to achieve higher systemic concentration of a non-steroidal anti-inflammatory drug, proportionately higher concentrations of the enhancer of the invention may be required in the transdermal drug delivery system of the present invention, and the amount of non-steroidal anti-inflammatory drug included in the composition should be sufficient to provide the blood level desired.

The concentration of absorption/penetration enhancer may be in the range from 10-10,000 weight percent of absorption/penetration enhancer based upon the weight of non-steroidal anti-inflammatory drug. The ratio of penetration enhancer to non-steroidal anti-inflammatory drug may vary considerably and will be governed as much as anything, by the pharmacological results that are required to be achieved. In principle, it is desirable that as little absorption enhancer as possible is used. On the other hand, for some non-steroidal anti-inflammatory drugs, it may well be that the upper range of 10,000% by weight will be required. It is preferred that the penetration enhancer and non-steroidal anti-inflammatory drug are in approximately equal proportions.

A particular advantage of the drug delivery system of the present invention is that patient compliance is improved as the system does not occlude the skin. As a result local irritation and allergic sensitisation problems arising from prolonged exposure of the skin to both the delivery system of occlusive transdermal patch devices and the adhesive used to affix these patches to the skin are reduced.

The following definitions apply through this description and the claims which follow.

The terms "percutaneous" and "transdermal" are used herein in the broadest sense to refer to being able to pass through unbroken skin.

The term "dermal penetration enhancer" is used herein in its broadest sense to refer to an agent which improves the rate of percutaneous transport of active agents across the skin or use and delivery of active agents to organisms such as animals, whether it be for local application or systemic delivery.

The term "non-occlusive" is used herein in its broadest sense to refer to not trapping or closing the skin to the atmosphere by means of a patch device, fixed reservoir, application chamber, tape, bandage, sticking plaster, or the like which remains on the skin at the site of application for a prolonged length of time.

The term "stratum corneum" is used herein in its broadest sense to refer to the outer layer of the skin, which is comprised of (approximately 15) layers of terminally differentiated keratinocytes made primarily of the proteinaceous material keratin arranged in a 'brick and mortar' fashion with the mortar being comprised of a lipid matrix made primarily from cholesterol, ceramides and long chain fatty acids. The stratum corneum creates the rate-limiting barrier for diffusion of the active agent across the skin.

The term "skin-depot" is used herein in its broadest sense to refer to a reservoir or deposit of active agent and dermal penetration enhancer within the stratum corneum, whether it be intra-cellular (within keratinocytes) or inter-cellular.

The term "volatile:non-volatile liquid vehicle" is used in the art to refer to a liquid pharmaceutical vehicle comprising a volatile liquid mixed with a non-volatile liquid vehicle, such as a dermal penetration enhancer. A system or vehicle comprising a volatile liquid mixed with a non-volatile dermal penetration enhancer when described herein is used in its broadest sense to include those systems known as volatile: non-volatile liquid vehicles.

Alkyl and alkoxy groups referred to herein may be either straight chain or branched. The term "lower alkyl" means alkyl groups containing from 1 to 5 carbon atoms. The term lower alkoxy has a similar meaning. The term "long chain alkyl" means alkyl groups containing from 5 to 18 carbon atoms, more preferably 6 to 18 carbon atoms. The term "halide" means fluoride, chloride, bromide or iodide. The term "heterocyclic ring" is herein defined to mean a ring of carbon atoms containing at least one hetero atom, and further the ring may be saturated or unsaturated to any allowable degree.

The term "sunscreen" is used herein in its broadest sense to refer to a chemical agent capable of filtering out ultraviolet light.

The drug delivery system of the present invention enables a wide range of non-steroidal anti-inflammatory drugs to be delivered through the skin to achieve a desired systemic effect. The drug delivery system preferably comprises the non-steroidal anti-inflammatory drug intimately mixed with a non-volatile dermal penetration enhancer and a volatile liquid. Where the drug delivery system is applied to the skin, the non-steroidal anti-inflammatory drug and non-volatile liquid are thermodynamically driven into the skin as the volatile liquid evaporates. Once within the skin the non-volatile liquid may either disrupt the lipid matrix and/or act as a solubilizer to allow an enhanced penetration rate of the non-steroidal anti-inflammatory drug through the skin and into the subject being treated. In this way, the dermal penetration enhancer acts as a vehicle and many systemic active non-steroidal anti-inflammatory drugs are able to be transdermally administered to an animal.

It is believed that the non-volatile dermal penetration enhancer is readily absorbed into the stratum corneum in sufficient quantities to form a reservoir or depot of the dermal penetration enhancer within the stratum corneum. The dermal penetration enhancer also contains the non-steroidal anti-inflammatory drug to be administered and as the dermal penetration enhancer crosses through the skin to form the skin-depot, the non-steroidal anti-inflammatory drug contained therein is transported through the skin and contained within the depot. These depots are believed to form within the lipid matrix of the stratum corneum wherein the lipid matrix creates a rate-limiting barrier for diffusion of the non-steroidal anti-inflammatory drug across the skin and allows the dermally administered non-steroidal anti-inflammatory drug to be systemically released over a period of time, usually up to 24 hours.

Once the volatile liquid of the drug delivery system has evaporated, driving the mixture of non-volatile dermal penetration enhancer and non-steroidal anti-inflammatory drug into the stratum corneum, the outer surface of the skin is then substantially free of non-steroidal anti-inflammatory drug and non-volatile dermal penetration enhancer. Normal touching, wearing of clothes, rinsing or even washing of the skin will not, to any significant extent, affect delivery of the non-steroidal anti-inflammatory drug or displace either the non-steroidal anti-inflammatory drug or the non-volatile dermal penetration enhancer, once the volatile liquid has evaporated.

This is in contrast to prior-art systems where supersaturated solutions are used to increase the rate of drug permeation across the skin. Such supersaturated solutions are susceptible of ready precipitation and require stabilization, such as with polymers, or protection from external surfaces or objects which may effect nucleation.

The rate of absorption of the non-steroidal anti-inflammatory drug via the stratum corneum is increased by the non-volatile dermal penetration enhancer. The non-steroidal anti-inflammatory drug may be dissolved or suspended in the dermal penetration enhancer at the time when it is being transported from the surface of the skin and into the stratum corneum. The performance of the dermal penetration enhancer to deliver a desired non-steroidal anti-inflammatory drug varies with differences in both the nature of the dermal penetration enhancer and the non-steroidal anti-inflammatory drug. It is understood that different dermal penetration enhancers may need to be selected to be appropriate for delivery of various non-steroidal anti-inflammatory drugs.

Diseases or conditions that may be treated by using the drug delivery system and methods of the present invention include, but are not limited to pain associated with musckuloskeletal disorders, arthritic pain, and other inflammatory conditions of joints and soft-tissue (e.g. muscle tissue).

The drug delivery system of the present invention may be applied to the skin by means of an aerosol, spray, pump-pack, brush, swab, or other applicator. Preferably, the applicator provides either a fixed or variable metered dose application such as a metered dose aerosol, a stored-energy metered dose pump or a manual metered dose pump. Preferably the drug delivery system is applied to the skin of the animal covering a delivery surface area between about 10 and 2000 cm$^2$, more preferably between about 10 and 400 cm$^2$, and most preferably between about 10 and 200 cm$^2$. The application is most preferably performed by means of a topical metered dose spray combined with an actuator nozzle shroud which together accurately control the amount and/or uniformity of the dose applied. One function of the shroud is to keep the nozzle at a pre-determined height above, and perpendicular to, the skin to which the drug delivery system is being applied. This function may also be achieved by means of a spacer-bar or the like. Another function of the shroud is to enclose the area above the skin in order to prevent or limit bounce-back and/or loss of the drug delivery system to the surrounding environment. Preferably the area of application defined by the shroud is substantially circular in shape.

The drug delivery system may be propelled by either pump pack or by the use of propellants such as hydrocarbons, hydro fluorocarbons, nitrogen, nitrous oxide, carbon dioxide or ethers, preferably dimethyl ether. The drug delivery system is preferably in a single phase system as this allows less complicated manufacture and ease of dose uniformity. It may also be necessary to apply a number of dosages on untreated skin to obtain the desired result.

DETAILED DESCRIPTION OF THE INVENTION

The invention will now be described with reference to the following examples and accompanying figure. The examples and figure are not to be construed as limiting the invention in any way. They are included to further illustrate the present invention and advantages thereof.

In the examples, the effectiveness of the penetration enhancers are illustrated by measuring the skin penetration of formulations of a number of representative non-steroidal anti-inflammatory drugs with the dermal penetration enhancers. Also, the skin penetration of non-steroidal anti-inflammatory drugs are measured with other prior art penetration enhancers as well as formulations of the non-steroidal anti-inflammatory drugs with common adjuvants, which serve as control formulations. The comparisons generally consist of measuring the relative penetration through shed snake skin of the various formulations. In every case, those formulations which contain the dermal penetration enhancers deliver more of the non-steroidal anti-inflammatory drug through the skin than the corresponding control formulation or commercial preparation.

EXAMPLE 1

Figure 1:
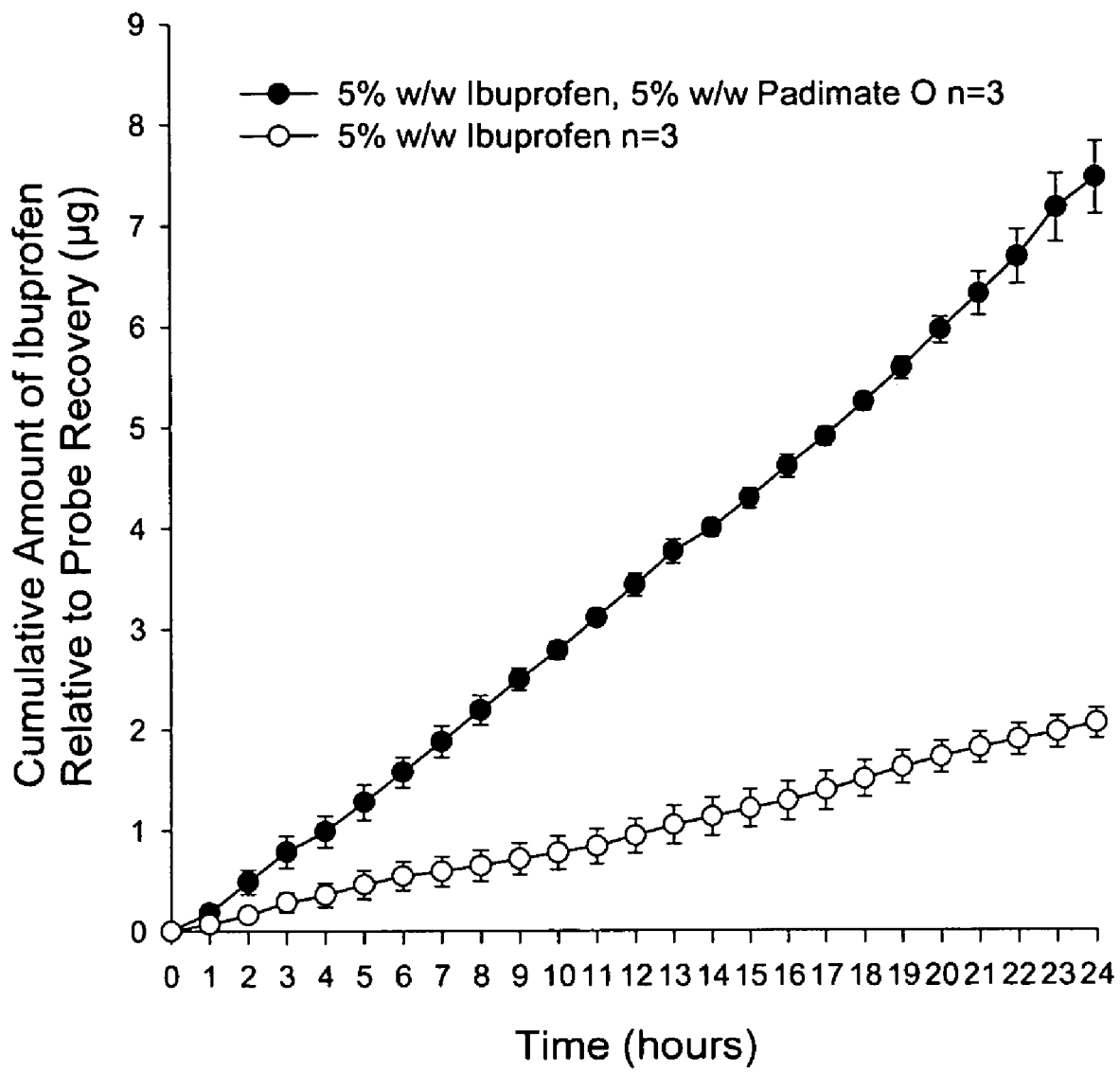
FIG. 1 Shows the cumulative amount of ibuprofen penetrating into the microdialysis probe, adjusted for individual probe recovery over a 24 hour period.

Enhanced skin penetration of ibuprofen using Padimate O in a transdermal gel composition (Composition 3B). FIG. 1 shows the cumulative amount of ibuprofen penetrating into the microdialysis probe, adjusted for individual probe recovery over a 24 hour period.

As shown in FIG. 1, the addition of the safe sunscreen ester dermal penetration enhancer, Padimate O, causes a marked 3.5-fold increase in the in vivo transdermal delivery of ibuprofen across the skin ($p<0.05$).

The diffusion of ibuprofen from the gel formulations is measured in vivo in conscious rats. Briefly, linear microdialysis probes are inserted in the subcutaneous region on the dorsum of Sprague Dawley rats. These probes allow sampling of the extracellular fluid for exogenous or endogenous substances (Ungerstedt 1991: Microdilysis—principles and applications for studies in animals and man. *Journal of Internal Medicine* 230: 365-373 Ungerstedt 1991) and thus once the ibuprofen penetrates the skin it is collected in the dialysate flowing through the probe. The dialysate is collected in hourly intervals for 24 hours and analysed directly by RP-HPLC.

Samples are analysed for ibuprofen directly by RP-HPLC using the following conditions: Column—Waters Spherisorb $C_{18}$ column (4.6 mm×250 mm); Mobile phase—55% Acetonitrile, 45% water made to pH 3.5 with orthophosphoric acid; Flow rate 1.5 mL/min; Absorbance—210 nm; and Injection volume—20 µL.

In vitro Skin Diffusion Measurements Shed Snake Skin

The Children's python shed snake skin is obtained during natural shedding and the dorsal skin is used. Shed snake skin has been shown to be a suitable model membrane for human skin by Itoh, et al., "Use of Shed Snake Skin as a Model Membrane for In Vitro Percutaneous Penetration Studies: Comparison with Human Skin", Pharm. Res., 7(10), 1042-1047, 1990; and Rigg, et al., "Shed Snake Skin and Hairless Mouse Skin as Model Membranes for Human Skin During Permeation Studies", J. Invest. Dermatol., 94; 235-240,1990.

Full Thickness Skin

The animals for these investigations are obtained from the animal house at the Victorian College of Pharmacy, Monash University, Parkville, Australia.

Hairless Mouse Skin

Hairless mice of 4-8 weeks of age are used. The mouse skin is excised and full-thickness skin is isolated from the torso, the subcutaneous fat and connective tissue is removed and the skin is cut into circles of 2.0 cm$^2$, and then is placed into diffusion cells for flux measurements.

In vitro Skin Diffusion Experiments in Horizontal Diffusion Cells

A modified stainless steel flow-through diffusion cell assembly based on that first shown by Cooper in J. Pharm. Sci. 73(8), 1984, is used to perform the experiments on diffusion of the drugs from various donor compositions through the skin (either snake or hairless mouse). The cell consists of an upper section and a lower section. A stainless steel wire mesh support is housed in a recess in the lower section of the cell. The skin sample, cut into a circle, is gently placed over the support and the two sections of the cells are secured together by screws, using the locating holes, to form a tight seal. An aperture in the upper section of the cell, which has an area of 0.79 cm$^2$ (0.5 cm in diameter), forms a well above the skin into which the topical formulation is applied. In most cases 400 microL of formulation, solution or suspension containing the drug substance to be tested is applied evenly over the skin. The bottom section of the cell is provided with inlet and outlet tubes which connect to the bottom of the recess and through which a receptor solution is pumped by a microcassette peristaltic pump (Watson Marlow, UK) (not shown) at a constant flow rate to maintain sink conditions. The receptor solution consists of 50% propylene glycol in water, is made isotonic with 0-9% sodium chloride and is preserved with 0-1% sodium azide or 0.1% sodium fluoride. To prevent air bubbles forming under the skin, the wire mesh ensures turbulent receptor flow. The recess is filled with receptor solution prior to placing the skin in the cell. The receptor solution is degassed by spraying the solution into fine droplets under vacuum while stirring at 40 degrees C. Degassing is repeated three times. These precautions eliminate the need for a bubble chamber in the diffusion cell. The diffusion cells are set on a hollow metal heater bar which maintains normal skin temperature of 32 degrees C. (±0.5 degrees C.) by means of heated, circulating water (Thermomix, Braun, Germany). Each diffusion cell has its receptor solution collected via tube into polyethylene vials (6 ml liquid scintillation vials, Packard instruments, Netherlands) at two or four hour intervals for 24 hours, by means of an automated rotating fraction collector (Retriever II, ISCO, Australia). The amount of drug in each vial containing receptor solution is determined by reverse phase HPLC. Prior to analysis each vial is weighed with an analytical balance (Mettler AT261, Australia) and the volume is calculated from the density of the receptor solution which is 1.0554 g/cm$^3$ at 22 degrees C.

The concentration of applied drug in each diffusion cell sample is measured using high pressure liquid chromatography (HPLC). The receptor solution is assayed neat, with 20 microL injected (WISP 712 autoinjector, Waters, Australia) into a freshly prepared and degassed (by filtering) mobile phase. Each drug is separated using a pre column fitted with a C18 insert and a .mu.Bondapak C18 (30 cm.times.3.9 nm) HPLC column (Waters). Absorbance is measured at the appropriate wavelength using a Waters tuneable absorbance detector and peak area is plotted and integrated using a Shimadzu C-R3A chromatic integrator. The results for each experiment are the average values of four replicate diffusion cells unless stated otherwise. The assay conditions for each different drug are given in each example.

EXAMPLE 2

The in vitro diffusion cell method described above is used to compare the penetration of 400 microL of 2% w/v ketoprofen in 70% v/v aqueous ethanol applied to the shed snake skin following the application of 400 microL of the different dermal penetration enhancers in a 2% v/v solution in 70% ethanol, 2 hours prior to the application of the ketoprofen. The control experiment involves application of 400 microL of 70% aqueous ethanol alone for 2 hours, followed by application of 400 microL of the 2% ketoprofen solution. Samples are assayed according to the method described previously. The detection wavelength is 255 nm and the mobile phase consists of acetonitrile:water (55:45) made to pH 3.0 with orthophosphoric acid (BDH, Australia). Table 1 shows the mean flux of ketoprofen across the snake skin over 24 hours as determined by the linear regression of the cumulative amount of ketoprofen crossing the skin versus time (Units=microg/cm$^2$.h).

TABLE 1

| Enhancer type | Mean flux +/− std error (microg/cm$^2$·h) | p value relative to control | Enhancement ratio |
|---|---|---|---|
| Control - no enhancer, n = 9 | 0.96 ± 0.18 | — | — |
| Azone, n = 2 | 2.58 ± 0.23 | 0.0029 | 2.7 |
| Octyl dimethyl PABA, n = 3 | 2.25 ± 0.14 | 0.0068 | 2.3 |
| Octylmethoxy cinnamate, n = 3 | 3.22 ± 0.28 | 0.0003 | 3.35 |
| Octyl salicylate, n = 2 | 27.66 ± 5.26 | <0.0070 | 28.81 |

NB. Enhancement ratio = mean flux enhancer/mean flux control

Statistical significance is determined by means of a Student's t-test. Azone is selected as the standard penetration enhancer for comparison since it has been widely used in previous percutaneous penetration experiments.

EXAMPLE 3

The same protocol as Example 2 is repeated, except the dermal penetration enhancers are included in the ketoprofen formulation, such that 400 microL of 2% w/v ketoprofen and 2% v/v dermal penetration enhancer in 70% v/v aqueous ethanol is applied to the skin from the start of the diffusion experiment.

Table 2 shows the mean flux of ketoprofen across the snake skin over 24 hours.

TABLE 2

| Enhancer type | Mean flux +/− std error (microg/cm$^2$·h) | p value relative to control | Enhancement ratio |
|---|---|---|---|
| Control - no enhancer, n = 10 | 0.78 ± 0.07 | — | — |
| Azone, n = 2 | 2.84 ± 0.11 | <0.0001 | 3.6 |
| Octyl dimethyl PABA, n = 2 | 2.71 ± 0.18 | <0.0001 | 3.5 |
| Octylmethoxy cinnamate, n = 2 | 2.08 ± 0.39 | 0.0413 | 2.7 |
| Octyl salicylate, n = 4 | 61.68 ± 14.89 | <0.0059 | 79.1 |

These results demonstrate the ability of the dermal penetration enhancers to be applied together with the non-steroidal anti-inflammatory drug within the same formulation to achieve percutaneous absorption enhancement.

EXAMPLE 4

Table 3 shows the median amount (□g/cm$^2$) of ibuprofen penetrating across full-thickness hairless mouse skin in vitro when 400 microL of a 2% w/v ibuprofen and 2% v/v dermal penetration enhancer in 70% v/v aqueous ethanol is applied. Again, Azone is selected as the standard for comparison and the control formulation contains no penetration enhancer. The detection wavelength is 210 nm and the mobile phase consists of acetonitrile:water (55:45) made to pH 3.0 with orthophosphoric acid.

TABLE 3

| Enhancer type | after 12 hours | after 24 hours |
| --- | --- | --- |
| Octyl methoxycinnamate 2% v/v | 1099* | 2458* |
| Octyl dimethyl PABA 2% v/v | 1123* | 2981* |
| Azone 2% v/v | 1036* | 2684* |
| Control (no enhancer) | 474 | 1819 | n = 8, *statistically significantly different from control, p < 0.05 following ANOVA on Ranks.

EXAMPLE 5

Figure 2:
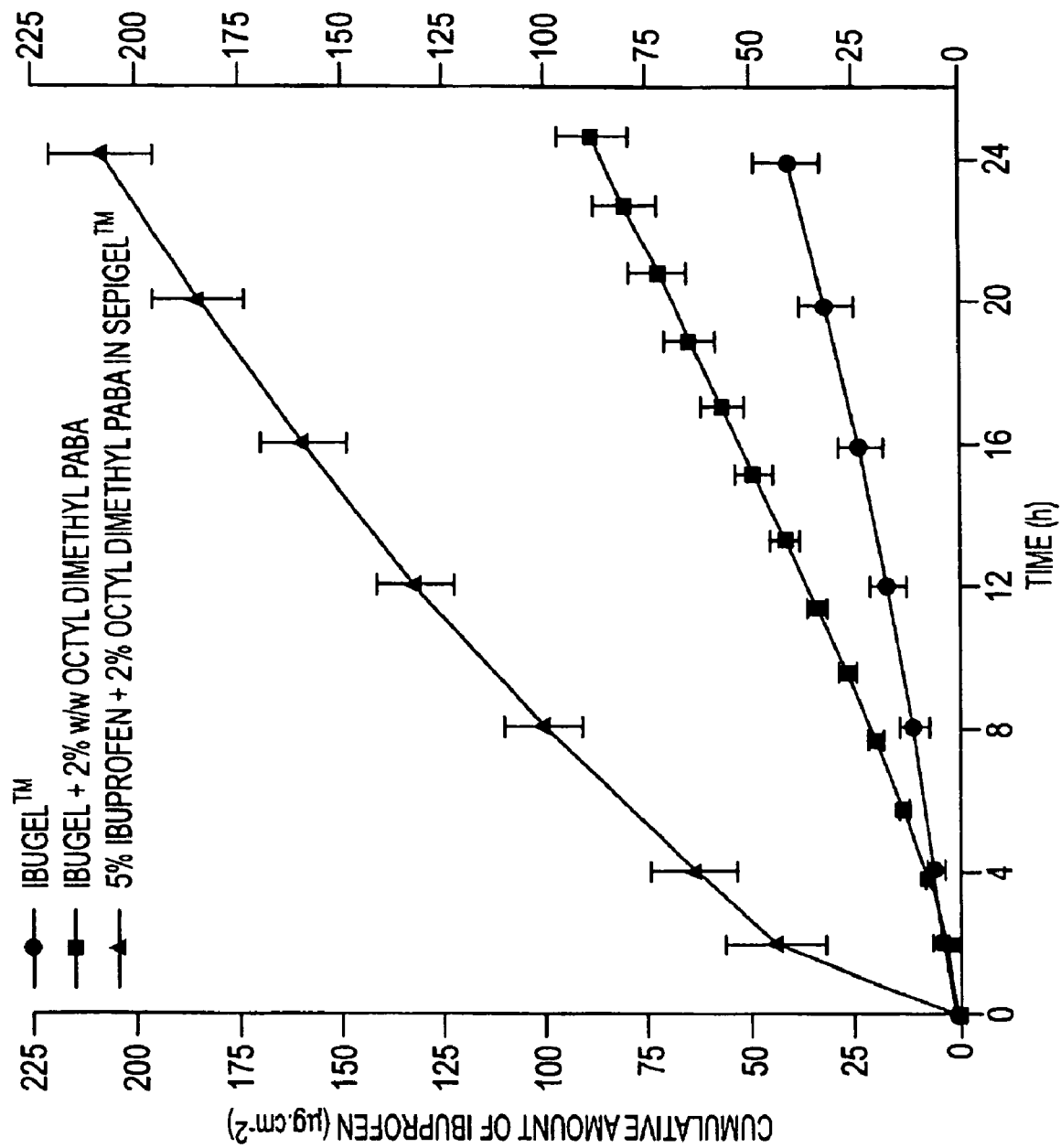
FIG. 2 Shows the cumulative amount of ibuprofen transferring across shed snake skin versus time for gel formulations of ibuprofen (5 mg of each gel was applied to the skin).

FIG. 2 shows the cumulative amount of ibuprofen transferring across shed snake skin versus time for gel formulations of ibuprofen. 5 mg of each gel is applied to the skin. Samples are assayed by the HPLC method mentioned in Example 4. The gels are made to a final concentration of 5% w/w ibuprofen and 2% w/w dermal penetration enhancer by first dissolving them in 50% v/v aqueous ethanol then adding 2% w/w Sepigel 305™ (SEPPIC, Paris, France) as a gelling agent and stirring at room temperature until a gel is formed. This formulation is compared with the commercial IBUGEL™ (Dermal Laboratories, UK) formulation which contains 5% w/w ibuprofen in an ethanolic gel base formed with carbopol. As well, 2% w/w dermal penetration enhancer is added to the IBUGEL by simple mixing. The ibuprofen contents of each gel are determined by HPLC and are found to be 5.02, 5.75 and 5.43 mg/g for the gel using Sepigel-305™ and enhancer, the IBUGEL and the IBUGEL with enhancer, respectively.

Both the cumulative amounts at 12 an 24 h and the mean flux over 24 h are significantly greater (p<0.05) for both the enhanced gel formulations when compared to the commercial IBUGEL formulation. The flux enhancement ratios are 6.15 and 2.61 for the gel using Sepigel-305™ and enhancer and the IBUGEL with enhancer (n=3) respectively when compared to the IBUGEL (p<0.05).

EXAMPLE 6

Table 4 shows the mean flux over 24 h of ketoprofen from a transdermal patch using the enhancer octyl salicylate compared with a control without enhancer. The patches are prepared by dissolving 300 mg of ketoprofen, 400 mg of penetration enhancer, 300 mg of polyethylene glycol 400 and 800 mg of hydroxypropylcellulose in 20 mL of ethanol and stirring until viscous. This is then poured onto a clean glass plate and dried at 40 degrees Celsius for 1 h. The thickness of this film is approximately 1 mm. Circles of 0.8 $cm^2$ are cut out of this matrix and are stuck onto the middle of 2.0 $cm^2$ circles of OPSITE™ adhesive bandage. This patch is stuck onto 2.0 $cm^2$ pieces of snake skin and is placed in the diffusion cell. The ketoprofen content of each patch formulation is determined by HPLC in triplicate and is found to be 6.99±0.30 mg/$cm^2$ and 6.76±0.24 mg/$cm^2$, for the control and octyl salicylate patches respectively (mean content±std error, n=4).

TABLE 4

| Enhancer type | Mean flux +/− Std error (microg/$cm^2$ · h) | p value relative to control | Enhancement ratio |
| --- | --- | --- | --- |
| Control - no enhancer | 0.47 ± 0.04 | — | — |
| Octyl salicylate | 11.70 ± 0.65 | <0.0001 | 25.2 |

EXAMPLE 7

Topical spray compositions

| Composition 7A | | Composition 7B | |
| --- | --- | --- | --- |
| Component | Amount | Component | Amount |
| Ibuprofen | 4% w/v | Ibuprofen | 4% w/v |
| Octyl salicylate | 5% w/v | Padimate O | 6% w/v |
| Aqueous ethanol (95% v/v) | to 100 mL | Aqueous ethanol (95% v/v) | to 100 mL |

EXAMPLE 8

Topical gel compositions

| Composition 8A | | Composition 8B | |
| --- | --- | --- | --- |
| Component | Amount | Component | Amount |
| Ibuprofen | 2% w/v | Ibuprofen | 2% w/v |
| Octyl salicylate | 1% w/v | Padimate O | 2% w/v |
| Carbopol | 0.9% w/v | Carbopol | 0.9% w/v |
| 0.1N NaOH | 4.72% w/v | 0.1N NaOH | 4.92% w/v |
| Aqueous ethanol (70% v/v) | to 100 mL | Aqueous ethanol (70% v/v) | to 100 mL |

EXAMPLE 9

Topical lotion compositions

| Composition 9A | | Composition 9B | |
| --- | --- | --- | --- |
| Component | Amount | Component | Amount |
| Ibuprofen | 2% w/v | Ibuprofen | 2% w/v |
| Octyl salicylate | 2% w/v | Padimate O | 3% w/v |
| Hydroxy propyl cellulose | 1.5% w/v | Ethyl cellulose | 1.5% w/v |
| Aqueous ethanol (90% v/v) | to 100 mL | Aqueous ethanol (90% v/v) | to 100 mL |

We claim:
1. A transdermal drug delivery system comprising:
(a) a therapeutically effective amount of a non-steroidal anti-inflammatory drug;
(b) at least one dermal penetration enhancer, which is a safe skin-tolerant ester sunscreen of formula (I):

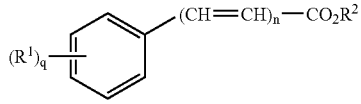

wherein
- R¹ is hydrogen, lower alkyl, lower alkoxy, halide, hydroxy or NR³R⁴;
- R² is a $C_8$ to $C_{18}$ alkyl;
- R³ and R⁴ are each independently hydrogen, lower alkyl or R³ and R⁴ together with the nitrogen atom to which they are attached form a 5- or 6-membered heterocyclic ring;
- n is 0 or 1, and
- q is 1 or 2, wherein, when n is 0 and R¹ is NR³R⁴, then NR³R⁴ is para-substituted, and wherein said dermal penetration enhancer is present in an amount of from about 10 to about 10,000 wt % based on the weight of the non-steroidal anti-inflammatory drug; and (c) at least one volatile liquid.

2. The transdermal drug delivery system according to claim 1, wherein the dermal penetration enhancer is octyl salicylate.

3. The transdermal drug delivery system according to claim 1, wherein the volatile liquid selected from the group consisting of ethanol, isopropanol, and a mixture thereof.

4. The transdermal drug delivery system according to claim 1, comprising on a weight basis:
   (a) from about 1 to about 15% of said non-steroidal anti-inflammatory drug;
   (b) from about 1 to about 10% of said at least one dermal penetration enhancer; and
   (c) from about 75 to about 98% of said volatile liquid.

5. The transdermal drug delivery system according to claim 1, wherein the non-steroidal anti-inflammatory drug is selected from the group consisting of acemetacin, amtolmetin, azapropazone, benorilate, benoxaprofen, benzydamine hydrochloride, bromfenal, bufexamac, butibufen, carprofen, celecoxib, choline salicylate, dipyone, droxicam, etodolac, etofenamate, etoricoxib, felbinac, fentiazac, floctafenine, indoprofen, isoxicam, lomoxicam, loxoprofen, licofelone, fepradinol, magnesium salicylate, meclofenamic acid, meloxicam, morniflumate, niflumic acid, nimesulide, oxaprozen, piketoprofen, priazolac, pirprofen, propyphenazone, proquazone, rofecoxib, salalate, sodium salicylate, sodium thiosalicylate, suprofen, tenidap, tiaprofenic acid, trolamine salicylate, and zomepirac.

6. The transdermal drug delivery system according to claim 1, wherein the non-steroidal anti-inflammatory drug is selected from the group consisting of aclofenac, aloxiprin, aproxen, aspirin, diflunisal, fenoprofen, indomethacin, mefenamic acid, piroxicam, phenylbutazone, salicylamide, salicylic acid, sulindac, desoxysulindac, tenoxicam, tramadol, ketoralac, clonixin, fenbufen, benzydamine hydrochloride, meclofenamic acid, flufenamic acid and tolmetin.

7. The transdermal drug delivery system according to claim 1, wherein the non-steroidal anti-inflammatory drug is piroxicam.

8. The transdermal drug delivery system according to claim 1, wherein the non-steroidal anti-inflammatory drug is selected from the group consisting of ibuprofen, naproxen, flurbiprofen, diclofenac, and ketoprofen.

9. The transdermal drug delivery system according to claim 8, comprising on a weight basis:
   (a) from about 1 to about 15% ibuprofen;
   (b) from about 1 to about 10% octyl salicylate; and
   (c) from about 75 to about 98% Alcohol USP (95% ethanol).

10. The transdermal drug delivery system according to claim 8, comprising on a weight basis:
    (a) from about 1 to about 5% ibuprofen;
    (b) from about 1 to about 5% octyl salicylate; and
    (c) from about 45 to about 90% of a volatile liquid selected from the group consisting of ethanol, isopropanol, and a mixture thereof;
    (d) from about 5 to about 45% water; and
    (e) from about 0.5 to about 5% of a thickening agent.

11. A method for administering at least one systemic or locally acting non-steroidal anti-inflammatory drug to an animal which comprises applying an effective amount of the non-steroidal anti-inflammatory drug in the form of the drug delivery system according to claim 1.

12. The method according to claim 11, wherein the non-steroidal anti-inflammatory drug is selected from the group consisting of acemetacin, amtolmetin, azapropazone, benorilate, benoxaprofen, benzydamine hydrochlorie, bromfenal, bufexamac, butibufen, carprofen, celecoxib, choline salicylate, dipyone, droxicam, etodolac, etofenamate, etoricoxib, felbinac, fentiazac, floctafenine, indoprofen, isoxicam, lomoxicam, loxoprofen, licofelone, fepradinol, magnesium salicylate, meclofenamic acid, meloxicam, morniflumate, niflumic acid, nimesulide, oxaprozen, piketoprofen, priazolac, pirprofen, propyphenazone, proquazone, rofecoxib, salalate, sodium salicylate, sodium thiosalicylate, suprofen, tenidap, tiaprofenic acid, trolamine salicylate, and zomepirac.

13. The method according to claim 12, wherein the non-steroidal anti-inflammatory drug is piroxicam.

14. The method according to claim 11, wherein the non-steroidal anti-inflammatory drug is selected from the group consisting of aclofenac, aloxiprin, aproxen, aspirin, diflunisal, fenoprofen, indomethacin, mefenamic acid, piroxicam, phenylbutazone, salicylamide, salicylic acid, sulindac, desoxysulindac, tenoxicam, tramadol, ketoralac, clonixin, fenbufen, benzydamine hydrochloride, meclofenamic acid, flufenamic acid and tolmetin.

15. The method according to claim 11, wherein the non-steroidal anti-inflammatory drug is selected from the group consisting of ibuprofen, naproxen, flurbiprofen, diclofenac, and ketoprofen.

16. The method according to claim 11, wherein the drug delivery system is applied to the skin of the animal covering a delivery surface area between about 10 and 2000 $cm^2$.

17. The method according to claim 11, wherein the drug delivery system is applied to the skin of the animal covering a delivery surface area between about 10 and 400 $cm^2$.

18. The method according to claim 11, wherein the drug delivery system is applied to the skin of the animal covering a delivery surface area between about 10 and 200 $cm^2$.

19. The method according to claim 11, wherein the drug delivery system is applied using a fixed or variable metered dose applicator.

* * * * *